United States Patent
Cooke et al.

(10) Patent No.: US 7,160,904 B2
(45) Date of Patent: *Jan. 9, 2007

(54) NICOTINE IN THERAPEUTIC ANGIOGENESIS AND VASCULOGENESIS

(75) Inventors: John Cooke, Palo Alto, CA (US);
James Jang, San Bruno, CA (US);
Phillip Tsao, San Jose, CA (US);
Christopher Heescheen, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 10/147,389

(22) Filed: May 15, 2002

(65) Prior Publication Data
US 2002/0128294 A1 Sep. 12, 2002

Related U.S. Application Data

(62) Division of application No. 09/628,226, filed on Jul. 28, 2000, now Pat. No. 6,417,205.

(60) Provisional application No. 60/146,233, filed on Jul. 28, 1999.

(51) Int. Cl.
*A01N 43/40* (2006.01)
*A61K 31/44* (2006.01)
*A61K 35/78* (2006.01)

(52) U.S. Cl. .................. 514/343; 424/751

(58) Field of Classification Search ............. 424/725, 424/751; 514/343; 436/92

See application file for complete search history.

(56) References Cited

U.S. PATENT DOCUMENTS

| 4,725,609 A | 2/1988 | Kull, Jr. et al. |
| 5,318,957 A | 6/1994 | Cid et al. |
| 5,508,030 A | 4/1996 | Bierman |
| 5,547,965 A * | 8/1996 | Kr uger et al. ............. 514/342 |
| 5,840,693 A * | 11/1998 | Eriksson et al. ............. 514/12 |
| 5,866,561 A | 2/1999 | Ungs |
| 5,869,037 A | 2/1999 | Crystal et al. |
| 6,417,205 B1 * | 7/2002 | Cooke et al. ............... 514/343 |

FOREIGN PATENT DOCUMENTS

| AT | 409219 | 6/2005 |
| DE | 3645036 | 1/1989 |
| WO | WO 97/34605 | 9/1997 |
| WO | WO 99/35131 | 7/1999 |
| WO | WO 00/23062 | 4/2000 |

OTHER PUBLICATIONS

Belluardo, et al. (1998). "Acute intermittent nicotine treatment produces regional increases of basic fibroblast growth factor messenger RNA and protein in the tel- and diencephalon of the rat", *Neuroscience*, 83(3): 723-740.

Bornmyr, et al. (1991) "Thermography and laser—Doppler flowmetry for monitoring changes in finger skin blood upon cigarette smoking", *Clinical Physiology*, vol. 11: 135-141.

(Continued)

*Primary Examiner*—Michele Flood
(74) *Attorney, Agent, or Firm*—Paula A. Borden; Bozicevic, Field & Francis, LLP

(57) ABSTRACT

The invention features methods for induction of angiogenesis by administration of nicotine or other nicotine receptor agonist. Induction of angiogenesis by the methods of the invention can be used in therapeutic angiogenesis in, for example, treatment of ischemic syndromes such as coronary or peripheral arterial disease.

4 Claims, 7 Drawing Sheets

Nicotine

Epibatidine

ABT-154

Hexamethonium

Mecamylamine

OTHER PUBLICATIONS

Carty, et al. (1996). "Nicotine and cotinine stimulate secretion of basic fibroblast growth factor and affect expression of matrix metalloproteinases in cultured human smooth muscle cells", *J. of Vascular Surgery*, vol. 24(6): 927-934.

Damaj, et al. (1998). "Antinociceptive responses to nicotinic acetylcholine receptor ligands after systemic and intrathecal administration in mice", *J. of Pharmacology and Experimental Therapeutics*, vol. 284(3): 1058-1065.

Decker, et al. (1999) "Therapeutic potential of neuronal nicotinic acetylcholine receptor agonists as novel analgesics", *Biochem. Pharm.*, vol. 58: 917-923.

Folkman, et al. (1996). "Blood vessel formation: What is its molecular basis?", *Cell*, vol. 87: 1153-1155.

Grando, et al. (1995) "A nicotinic acetylcholine receptor regulating cell adhesion and motility is expressed in human keratinocytes", *J. Invest. Dermatol.*, vol. 105: 774-781.

Grando, et al. (1996) "Activation of keratinocyte nicotinic cholinergic receptors stimulates calcium influx and enhances cell differentiation", *J. Invest. Dermatol.*, vol. 107: 412-418.

Grando, et al. (2000) "Nicotine and Pemphigus", *Arch Dermatol*, 136:1269.

Haas, et al. (1992) "Jean Nicot 1530-1600", *J. Neurol Neurosurg. Psychiatry*, vol. 55: 430.

Hanahan et al. (1996) "Patterns and emerging mechanisms of the angiogenic switch during tumorigenesis", *Cell*, vol. 86: 353-364.

Kanekura, et al. "Successful treatment of pyoderma gangrenosum with nicotine chewing gum", *Letters to the Editor*, pp. 704-705.

Kanekura, et al. (1995) "Nicotine for pyoderma gangrenosum", *Lancet* 345:1058.

Lopez- Arrieta et al. (2000), "Nicotine for Alzheimer's disease", *Cochrane Database Syst Rev*, (2)CD001749.

Macklin, et al. (1998). "Human vascular endothelial cells express functional nicotinic acetylcholine receptors", *J. of Pharmacology and Experimental Therapeutics*, vol. 287: 435-439.

Moffett, et al, (1998). "Increased tyrosine phosphorylation and novel *cis*-acting element mediate activastion of the fibroblast growth factor-2 (FGF-2) gene by nicotinic acetylcholine receptor, New mechanism for trans-synaptic regulation of cellular development and plasticity", *Molecular Brain Res.*, vol. 55: 293-305.

Møller, et al. (2002) "Effect of preoperative smoking intervention on postoperative complications: A randomized clinical trial", *Lancet*, vol. 359: 144-177.

Pullan, et al (1994) "Transdermal nicotine for active ulcerative colitis", *New England Journal of Medicine*, vol. 330: 811-815.

Sandborn (1999). "Nicotine therapy for ulcerative colitis: A review of rationale, mechanisms, pharmacology, and clinical results", *American J. of Gastroenterology*, vol. 94(5): 1161-1171.

Schneid, et al. "Nicotine patches for aphthous ulcers due to Behcet's syndrome", *New England Journal of Medicine*, 2000343:1816-1817.

Tonnesen, et al. (1991) "A double-blind trial of a 16-hour transdermal nicotine patche in smoking cessation", *New England Journal of Medicine*, 325:311-315.

Usuki, et al. (1998) "Effects of nicotine on peripheral cutaneous blood flow and skin temperature", *J. Dermatol. Sci.*, vol. 16: 173-181.

Vieregge, et al. "Transdermal nicotine in PD: a randomized, double-blind, placebo controlled study", *Neurology* 2001, 57:1032-1035.

Villablanca (1998). "Nicotine stimulates DNA synthesis and proliferation in vascular endothelial cells in vitro", *American Physiological Society*, pp. 2089-2098.

Volm, et al. (1999). "Angiogenesis and cigarette smoking in squamous cell lung carcinomas: an Immunohistochemical study of 28 cases", *Anticancer Research*, vol. 19: 333-336.

Westerman, et al. (1993) "The role of skin nociceptive afferent nerves in blister healing", *Clinical and Experimental Neurology*, vol. 30; 39-60.

Yancopoulos, et al. (1998). "Vasculogenesis, angiogenesis, and growth factors: Ephrins enter the fray at the border"*Cell*, vol. 93: 661-664.

Heeschen, Christopher et al., "Nicotine is an agent of angiogenesis: Role of nitric oxide and prostacyclin" Journal of American College Cardiology, vol. 35, No. 2, Suppl. A, Feb. 2000, pp. 545A-546A XP001180280, 29th Annual Scientific Session of the American College of Cardiology, Anaheim, CA, USA Mar. 12-15, 2000, ISSN: 0735-1097.

* cited by examiner

FIG. 1

Epibatidine

Nicotine

ABT-154

Mecamylamine

Hexamethonium

NICOTINE IN THERAPEUTIC ANGIOGENESIS AND VASCULOGENESIS

CROSS-REFERENCE TO RELATED APPLICATIONS

This application is a divisional application of U.S. patent application Ser. No. 09/628,226, filed Jul. 28, 2000, now U.S. Pat. No. 6,417,205, which application claims the benefit of U.S. Provisional Application Ser. No. 60/146,233, filed Jul. 28, 1999, which applications are incorporated herein by reference.

FIELD OF THE INVENTION

The invention relates generally to the field of regulation of angiogenesis and vasculogenesis, particularly to induction of angiogenesis to promote growth of new vasculature.

BACKGROUND OF THE INVENTION

Angiogenesis and vasculogenesis are processes involved in the growth of blood vessels. Angiogenesis is the process by which new blood vessels are formed from extant capillaries, while vasculogenesis involves the growth of vessels deriving from endothelial progenitor cells. Angiogenesis and vasculogenesis, and the factors that regulate these processes, are important in embryonic development, inflammation, and wound healing, and also contribute to pathologic conditions such as tumor growth, diabetic retinopathy, rheumatoid arthritis, and chronic inflammatory diseases (see, e.g., U.S. Pat. No. 5,318,957; Yancopoulos et al. (1998) Cell 93:661–4; Folkman et al. (1996) Cell 87;1153–5; and Hanahan et al. (1996) Cell 86:353–64).

Both angiogenesis and vasculogenesis involve the proliferation of endothelial cells. Endothelial cells line the walls of blood vessels; capillaries are comprised almost entirely of endothelial cells. The angiogenic process involves not only increased endothelial cell proliferation, but also comprises a cascade of additional events, including protease secretion by endothelial cells, degradation of the basement membrane, migration through the surrounding matrix, proliferation, alignment, differentiation into tube-like structures, and synthesis of a new basement membrane. Vasculogenesis involves recruitment and differentiation of mesenchymal cells into angioblasts, which then differentiation into endothelial cells which then from de novo vessels (see, e.g., Folkman et al. (1996) Cell 87:1153–5).

Several angiogenic and/or vasculogenic agents with different properties and mechanisms of action are well known in the art. For example, acidic and basic fibroblast growth factor (FGF), transforming growth factor alpha (TGF-α) and beta (TGF-β), tumor necrosis factor (TNF), platelet-derived growth factor (PDGF), vascular endothelial cell growth factor (VEGF), and angiogenin are potent and well-characterized angiogenesis-promoting agents. In addition, both nitric oxide and prostaglandin (a prostacyclin agonist) have been shown to be mediators of various angiogenic growth factors, such as VEGF and bFGF. However, the therapeutic applicability of some of these compounds, especially as systemic agents, is limited by their potent pleiotropic effects on various cell types.

Angiogenesis and vasculogenesis have been the focus of intense interest since these processes can be exploited to therapeutic advantage. Stimulation of angiogenesis and/or vasculogenesis can aid in the healing of wounds, the vascularizing of skin grafts, and the enhancement of collateral circulation where there has been vascular occlusion or stenosis (e.g., to develop a "biobypass" around an obstruction due to coronary, carotid, or peripheral arterial occlusion disease). There is an intense interest in factors that are well-tolerated by the subject, but that are of high potency in effecting stimulation of angiogenesis and/or vasculogenesis.

RELATED ART

Villablanca ((1998) "Nicotine stimulates DNA synthesis and proliferation in vascular endothelial cells in vitro," *J. Appl. Physiol.* 84:2089–98) studied the effects of nicotine on endothelial DNA synthesis, DNA repair, proliferation, and cytoxicity using cultures of bovine pulmonary artery endothelial cells in vitro.

The reference Carty et al. ((1996) "Nicotine and cotinine stimulate secretion of basic fibroblast growth factor and affect expression of matrix metalloproteinases in cultured human smooth muscle cells," *J Vasc Surg* 24:927–35) demonstrate that nicotine stimulates vascular smooth muscle cells to produce fibroblast growth factor, and also upregulates the expression of several matrix metalloproteinases. The investigators propose that these data demonstrate mechanisms by which smoking may cause atherosclerosis and aneurysms.

The reference by Belluardo et al. ((1998) Acute intermittent nicotine treatment produces regional increases of basic fibroblast growth factor messenger RNA and protein in the tel-and diencephalon of the rat," *Neuroscience* 83:723–40) reported that nicotine stimulates the expression of fibroblast growth factor-2 in rat brain, which the investigators propose may explain the neuroprotective effect of nicotine in the rat brain.

Moffett et al. (("Increased tyrosine phosphorylation and novel cis-actin element mediate activation of the fibroblast growth factor-2 (FGF-2) gene by nicotinic acetylcholine receptor. New mechanism for trans-synaptic regulation of cellular development and plasticity," *Mol Brain Res* 55:293–305) report that nicotine stimulates the expression of fibroblast growth factor-2 in neural crest-derived adrenal pheochromatocytes utilizing a unique transcriptional pathway that requires tyrosine phosphorylation. The authors propose that these findings suggest that activation of nicotine receptors may be involved in neural development.

Cucina et al. ((1999) "Nicotine regulates basic fibroblastic growth factor and transforming growth factor $\beta_1$ production in endothelial cells," *Biochem Biophys Res Commun* 257: 302–12) report that nicotine increases the release of bFGF, decreases the release of TGFβ1 from endothelial cells, and increases endothelial mitogenesis. The authors conclude that these effects may have a key role in the development and progression of atherosclerosis.

Volm et al. (1999) "Angiogenesis and cigarette smoking in squamous cell lung carcinomas: an immunohistochemical study of 28 cases." *Anticancer Res* 19(1A):333–6 reports that angiogenesis in lung tumors is linked to a patient's smoking habits.

Macklin et al. (1998) "Human vascular endothelial cells express functional nicotinic acetylcholine receptors," *J. Pharmacol. Exper. Therap.* 287:435–9 reports that endothelical cells express both functional nicotinic (neuronal type) and muscaxinic acetylcholine receptors.

U.S. Pat. Nos. 5,318,957; 5,866,561; and 5,869,037 describe use of various compounds (haptoglobin and estrogen) and methods (adenoviral-mediated gene therapy of adipocytes) to effect angiogenesis.

For recent reviews in the field of angiogenesis and vasculogenesis, see, e.g., Yancopoulos et al. (1998) *Cell* 93:661–4; Folkman et al. (1996) *Cell* 87;1153–5; and Hanahan et al. (1996) *Cell* 86:353–64.

SUMMARY OF THE INVENTION

The present invention features methods for induction of angiogenesis by administration of nicotine or other nicotine receptor agonist. Induction of angiogenesis by the methods of the invention can be used in therapeutic angiogenesis in, for example, treatment of ischemic syndromes such as coronary or peripheral arterial disease.

One object of the present invention to provide a method of controlling, particularly enhancing, angiogenesis, particularly with limited or no adverse effects.

Another object of the present invention is to provide a method of treating and preventing diseases and ailments involving angiogenesis such as myocardial and cerebral infarctions, mesenteric or limb ischemia, wounds, and vascular occlusion or stenosis.

Another object of this invention is to provide a method of enhancing angiogenesis to accelerate wound healing, or the vascularization of a skin graft, musculocutaneous flap or other surgically transplanted tissue; or to enhance the healing of a surgically created anastomosis.

These and other objects, advantages, and features of the invention will become apparent to those persons skilled in the art upon reading the details of the methods of the invention and compositions used therein as more fully described below.

DETAILED DESCRIPTION OF PREFERRED EMBODIMENTS

Before the present invention is described, it is to be understood that this invention is not limited to particular methodologies (e.g., modes of administration) or specific compositions described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nicotine receptor agonist" includes a plurality of such agonists and reference to "the nicotine receptor" includes reference to one or more receptors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "nicotine receptor agonist" is meant to encompass nicotine (which is understood from to include nicotine derivatives and like compounds) and other compounds that substantially specifically bind a nicotine receptor and provide a pharmacological effect, e.g., induction of angiogenesis. "Nicotine receptor agonists" encompass naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.).

Figure 1:
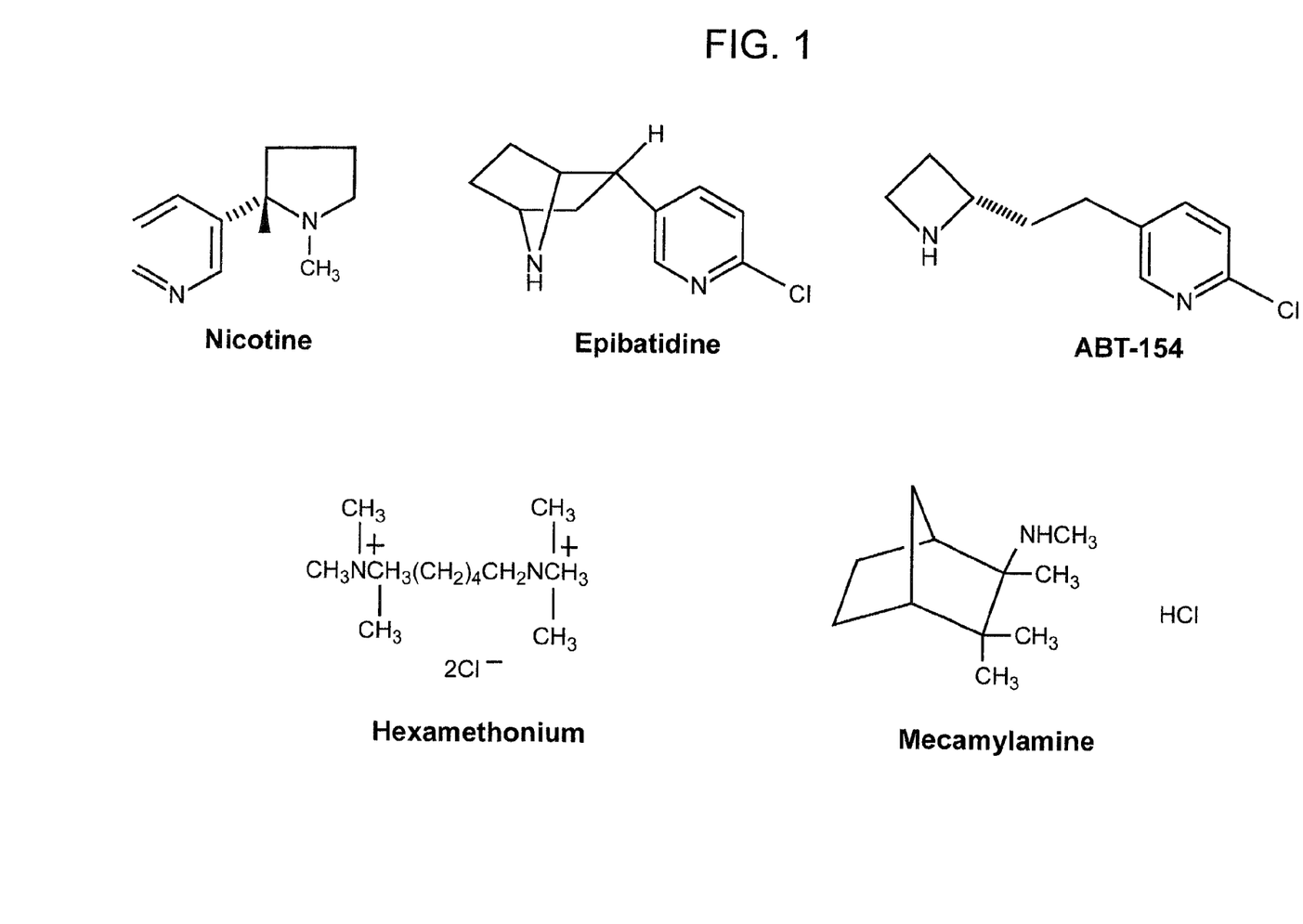
FIG. 1 provides the chemical structures for the nicotine receptor agonists nicotine, epibatidine, and ABT-154, and for the nicotine receptor antagonists hexamethonium and mecamylamine.

The term "nicotine" is intended to mean the naturally occurring alkaloid known as nicotine, having the chemical name S-3-(1-methyl-2-pyrrolidinyl)pyridine, which may be isolated and purified from nature or synthetically produced in any manner. This term is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23 and the formula shown in FIG. 1.

Unless specifically indicated otherwise, the term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof. A number of useful derivatives of nicotine are disclosed within the Physician's Desk Reference (most recent edition) as well as Harrison's Principles of Internal Medicine.

The term "nicotine receptor" as in "nicotine receptor agonist" is meant to encompass the classic pentameric protein of the nicotine receptor (formed by subunits which are symmetrically arranged around a central ion channel) as well as any protein comprising a nicotine binding site that stimulates angiogenesis upon binding to nicotine or other nicotine receptor agonist (e.g., the muscarinic acetylcholine receptor). Use of the term "nicotine receptor" in the phrase "nicotine receptor agonist" is not meant to limit the present invention to a theorized mechanism through which nicotine or other nicotine receptor agonists stimulate angiogenesis (e.g., by binding a nicotine receptor), but rather is a means of describing the types of compounds contemplated by the invention that can be used to facilitate stimulation of angiogenesis.

The terms "treatment", "treating" and the like are used herein to generally mean obtaining a desired pharmacologic and/or physiologic effect, e.g., stimulation of angiogenesis and/or vasculogenesis. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing the loss of a skin graft or a re-attached limb due to inadequate vascularization) from occurring in a subject who may be predisposed to the disease but has not yet been diagnosed as having it; (b) inhibiting the disease, e.g., arresting its development; or (c) relieving the disease (e.g., enhancing the development of a "bio-bypass" around an obstructed vessel to improve blood flow to an organ). In the context of the present invention, stimulation of angiogenesis and/or vasculogenesis is employed for subject having a disease or condition amenable to treatment by increasing vascularity and increasing blood flow.

By "therapeutically effective amount of a nicotine receptor agonist" is meant an amount of a nicotine receptor agonist effective to facilitate a desired therapeutic effect, e.g., a desired level of angiogenic and/or vasculogenic stimulation. The precise desired therapeutic effect will vary according to the condition to be treated.

By "isolated" is meant that the compound is separated from all or some of the components that accompany it in nature.

By "substantially pure nicotine receptor agonist" is meant that the nicotine receptor agonist has been separated from components that accompany it in nature. Typically, a nicotine receptor agonist is substantially pure when it is at least 60%, by weight, free from naturallyoccurring organic molecules with which it is naturally associated. Preferably, the preparation is at least 75%, more preferably at least 90%, and most preferably at least 99%, by weight, nicotine receptor agonist. A substantially pure nicotine receptor agonist can be obtained, for example, by extraction from a natural source (e.g., tobacco), by chemically synthesizing the compound, or by a combination of purification and chemical modification. Purity can be measured by any appropriate method, e.g., chromatography, mass spectroscopy, HPLC analysis, etc.

A nicotine receptor agonist is substantially free of naturally associated components when it is separated from those contaminants which accompany it in its natural state. Thus, a nicotine receptor agonist which is chemically synthesized or produced in a cellular system different from the cell from which it naturally originates will be substantially free from its naturally associated components.

Overview of the Invention

The present invention is based on the surprising discovery that nicotine induces angiogenesis. The inventors' initial inquiries were based on the clinical observation that smokers often have inadequate collateral development after coronary or peripheral arterial obstruction, i.e., the inventors suspected that nicotine might play a role in inhibition of angiogenesis. Accordingly, the inventors began by testing the local effects of nicotine in the disc angiogenesis system (DAS). Unexpectedly, the inventors discovered that nicotine was as or more potent as an angiogenic agent than any growth factor tested in this system, including Del1(Penta et al. (1999) *J Biol Chem* 274(16):11101–9) and bFGF. Additional studies revealed that the potent angiogenic effects of nicotine were mediated in part by products of the cycloxygenase cascade, and in part by the NO synthase pathway. Studies using the disc angiogenesis system suggested that nicotine may be useful for therapeutic angiogenesis. However, because angiogenesis is such a complex process, to demonstrate proof of principle that an agent has utility for therapeutic angiogenesis, the agent was tested in an animal model of disease that requires angiogenesis for its treatment. Accordingly, studies were performed in an animal model of arterial occlusion (the murine hindlimb ischemia model). Using this model of arterial occlusion, the inventors obtained compelling evidence that nicotine induces therapeutic angiogenesis.

Thus, the inventors have discovered that nicotine, a component of tobacco smoke, provides the basis of a new therapeutic approach to enhance angiogenesis in the treatment of coronary, peripheral, or other occlusive arterial diseases; and for the enhancement of wound healing and the improved vascularization of surgically transplanted tissues or organs(e.g., skin grafts or reattached limbs). In view of its similar or relatively increased angiogenic potency relative to other, conventional angiogenic agents, nicotine has significant advantage over current candidates as the basis of therapeutic angiogenesis. Moreover, the pharmacology and pharmacokinetics of nicotine have already been well-characterized in the context of smoking (e.g., in an effort to facilitate smoking cessation) and methods for slow release and local delivery have already been intensively investigated. Processes for the manufacture of nicotine and nicotine agonists are also well characterized. Furthermore, these small molecules are more easily synthesized and stored than complex angiogenic peptides.

Accordingly, the invention encompasses methods and compositions for stimulation of angiogenesis and/or vasculogenesis by administration of a nicotine receptor agonist. Of particular interest is the stimulation of angiogenesis and/or vasculogenesis in vivo to effect increase in blood flow, increased capillary density, and/or increased vascularity within, adjacent, or around an ischemic site.

Nicotine and Other Nicotine Receptor Agonists

The methods of the invention to stimulate angiogenesis are accomplished by administration of a nicotine receptor agonist, particularly nicotine, nicotine metabolite, or nicotine derivative. Methods for production of nicotine derivatives and analogues are well known in the art. See, e.g., U.S. Pat. No. 4,590,278; 4,321,387; 4,452,984; 4,442,292; and 4,332,945.

Additional nicotine receptor agonists of interest include, but are not necessarily limited to, naturally occurring plant alkaloids (e.g., lobeline, lobeline derivatives, and the like), which plant-derived compounds can be provided in a herbal preparation (e.g., in the form of dried tobacco leaves, in a poultice, in a botanical preparation, etc.), in isolated form (e.g., separated or partially separated from the materials that naturally accompany it), or in a substantially purified form. Other nicotine receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side-effects (e.g., Epidoxidine, ABT-154, ABT418, ABT-594; Abbott Laboratories (Damaj et al. (1998) *J. Pharmacol Exp. Ther.* 284:1058–65, describing several analogs of epibatidine of equal potency but with high specificity to the neuronal type of nicotinic receptors). Further nicotine receptor agonists of interest include, but are not necessarily limited to, N-methylcarbamyl and N-methylthi-O-carbamyl esters of choline (e.g., trimethylaminoethanol) (Abood et al. (1988) *Pharmacol. Biochem. Behav.* 30:403–8); acetylcholine (an endogenous ligand for the nicotine receptor); and the like.

Nicotine receptor agonists can also be readily identified using methods well known in the art. For example, the ability of a candidate nicotine receptor agonist can be screened for binding to a nicotine receptor in vitro, and the ability of the candidate agent to stimulate angiogenesis and/or vasculogenesis can be assessed in vivo (e.g., using the disc angiogenesis system (DAS), in the hindlimb ischemia model, etc.).

Pharmaceutical Compositions

Upon reading the present specification, the ordinarily skilled artisan will appreciate that the pharmaceutical compositions comprising a nicotine receptor agonist described herein can be provided in a wide variety of formulations. More particularly, the nicotine receptor agonist can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols. Where the nicotine receptor agonist is a naturally-occurring compound, the pharmaceutical composition can also be provided as an herbal preparation (e.g., in the form of tobacco leaves, as a poultice of plant matter, in a botanical preparation, etc.).

The nicotine receptor agonist formulation used will vary according to the condition or disease to be treated, the route of administration, the amount of nicotine receptor agonist to be administered, and other variables that will be readily appreciated by the ordinarily skilled artisan. In general, and as discussed in more detail below, administration of nicotine receptor agonists can be either systemic or local, and can be achieved in various ways, including, but not necessarily limited to, administration by a route that is parenteral, intravenous, intra-arterial, inter-pericardial, intramuscular, intraperitoneal, transdermal, transcutaneous, subdermal, intradermal, intrapulmonary, etc.

In pharmaceutical dosage forms, the nicotine receptor agonist may be administered in the form of their pharmaceutically acceptable salts, or they may also be used alone or in appropriate association, as well as in combination, with other pharmaceutically active compounds. The following methods and excipients are merely exemplary and are in no way limiting.

The nicotine receptor agonist can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Formulations suitable for topical, transcutaneous, and transdermal administration, e.g., to administer the nicotine receptor agonist directly to a wound, may be similarly prepared through use of appropriate suspending agents, solubilizers, thickening agents, stabilizers, and preservatives. Topical formulations may be also utilized with a means to provide continuous administration of nicotine or other nicotine receptor agonist by, for example, incorporation into slow-release pellets or controlled-release patches.

The nicotine receptor agonist can also be formulated in a biocompatible gel, which gel can be applied topically (e.g., to facilitate wound healing) or implanted (e.g., to provide for sustained release of nicotine receptor agonist at an internal treatment site). Suitable gels and methods for formulating a desired compound for delivery using the gel are well known in the art (see, e.g., U.S. Pat. Nos. 5,801,033; 5,827,937; 5,700,848; and MATRIGEL™).

For oral preparations, the nicotine receptor agonist can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The nicotine receptor agonist can be utilized in aerosol formulation to be administered via inhalation. The compounds of the present invention can be formulated into pressurized acceptable propellants such as dichlorodifluoromethane, propane, nitrogen and the like.

Furthermore, the nicotine receptor agonist can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and/or animal subjects, each unit containing a predetermined quantity of nicotine receptor agonist calculated in an amount sufficient to produce the desired angiogenic and/or vasculogenic effect in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In addition to one or more nicotine receptor agonists, the pharmaceutical formulations according to the invention can comprise or be administered in parallel with agents that enhance angiogenesis by enhancing nitric oxide (NO) levels (e.g., by enhancing activity of NO synthase, by enhancing release of NO, etc.) or prostacyclin levels (e.g., by enhancing activity prostacyclin synthase, by enhancing release of prostacyclin, etc.) Exemplary NO level-enhancing agents include, but are not necessarily limited to, L-arginine, L-lysine, and peptides enriched with these amino acids which can serve as substrates for NO; agents that preserve NO activity such as antioxidants (e.g., tocopherol, ascorbic acid, ubiquinone) or antioxidant enzymes (e.g., superoxide dismutase); and agents which can enhance NO synthase activity (e.g., tetrahydrobiopterin, or precursors for tetrahydrobiopterin (e.g., sepiapterin)); and the like. Exemplary prostacyclin level-enhancing agents include, but are not limited to precursors for prostacyclin such as eicosopentanoic acid and docosohexanoic acid; and prostanoids such as prostaglandin E1 and its analogues; and the like.

Alternatively or in addition, the pharmaceutical compositions according to the invention can comprise additional angiogenesis-inducing and/or vasculogenesis-inducing agents that act through pathways other than the nicotine receptor (e.g., VEGF, FGF (e.g., aFGF, bFGF), Del1, etc.).

Particularly where the nicotine receptor agonist is to be delivered for local application, e.g., by an intramuscular route, it may be desirable to provide the nicotine receptor agonist in a gel or matrix that can support angiogenesis, e.g., migration and proliferation of vascular cells into the matrix with endothelial tube formation. The gel or matrix can thus provide at least the initial substrate upon which new vessels form. For example, the gel or matrix can be extruded into an ischemic region to form a path for new blood vessel formation so as to bypass an obstruction in the area.

Induction of Angiogenesis in vivo

In order to accomplish stimulation of angiogenesis in vivo (e.g., as in the context of therapeutic angiogenesis), nicotine or other nicotine receptor agonists can be administered in any suitable manner, preferably with pharmaceutically acceptable carriers. One skilled in the art will readily appreciate that the a variety of suitable methods of administering nicotine or other nicotine receptor agonist in the context of the present invention to a subject are available, and, although more than one route can be used to administer a particular compound, a particular route can provide a more immediate, more effective, and/or associated with fewer side effects than another route. In general, a nicotine receptor agonist can be administered according to the method of the invention by, for example, a parenteral, intravenous, intra-arterial, interpericardial, intramuscular, intraperitoneal, transdermal, transcutaneous, subdermal, intradermal, or intrapulmonary route.

In order to avoid the side-effects associated with systemic nicotine, it may be preferable to administer nicotine locally (either alone or with agents to enhance the activity of the NO synthase or prostacyclin synthase pathways). Local administration can be accomplished by, for example, direct injection (e.g., intramuscular injection) at the desired treatment site, by introduction of the nicotine receptor agonist formulation intravenously at a site near a desired treatment site (e.g., into a vessel or capillary that feeds a treatment site), by intra-aterial or intra-pericardial introduction, by introduction (e.g., by injection or other method of implantation) of a nicotine receptor agonist formulation in a biocompatible gel or capsule within or adjacent a treatment site, by injection directly into muscle or other tissue in which increased blood flow and/or increased vascularity is desired, by rectal introduction of the formulation (e.g., in the form of a suppository to, for example, facilitate vascularization of a surgically created anastomosis after resection of a piece of the bowel), etc.

In one particular application of interest, the nicotine receptor agonist formulation is employed in a "biobypass" method, wherein instead of performing a more invasive procedure, such as a coronary bypass operation, a nicotine receptor agonist formulation is administered to induce growth of new blood vessels around the blocked region. In this embodiment, the nicotine receptor agonist formulation can be administered in the area of and/or proximate to the ischemic tissue to stimulate angiogenesis.

In some embodiments it may be desirable to deliver the nicotine receptor agonist directly to the wall of a vessel. One exemplary method of vessel wall administration involves the use of a drug delivery catheter, particularly a drug delivery catheter comprising an inflatable balloon that can facilitate delivery to a vessel wall. Thus, in one embodiment the method of the invention comprises delivery of a nicotine receptor agonist to a vessel wall by inflating a balloon catheter, wherein the balloon comprises a nicotine receptor agonist formulation covering a substantial portion of the balloon. The nicotine receptor agonist formulation is held in place against the vessel wall, promoting adsorption through the vessel wall. In one example, the catheter is a perfusion balloon catheter, which allows perfusion of blood through the catheter while holding the nicotine receptor agonist against the vessel walls for longer adsorption times. Examples of catheters suitable for nicotine receptor agonist application include drug delivery catheters disclosed in U.S. Pat. Nos. 5,558,642; U.S. Pat. No. 5,554,119; 5,591,129; and the like.

In another embodiment of interest, the nicotine receptor agonist formulation is delivered in the form of a biocompatible gel, which can be implanted (e.g., by injection into or adjacent a treatment site, by extrusion into or adjacent a tissue to be treated, etc.). Gel formulations comprising a nicotine receptor agonist can be designed to facilitate local release of the nicotine receptor agonist and other active agents for a sustained period (e.g., over a period of hours, days, weeks, etc.). The gel can be injected into or near a treatment site, e.g., using a needle or other delivery device. In one embodiment, the gel is placed into or on an instrument which is inserted into the tissue and then slowly withdrawn to leave a track of gel, resulting in stimulation of angiogenesis along the path made by the instrument. This latter method of delivery may be particularly desirable for, for the purpose of directing course of the biobypass.

In other embodiments it may be desirable to deliver the nicotine receptor agonist formulation topically, e.g., for localized delivery, e.g., to facilitate wound healing. Topical application can be accomplished by use of a biocompatible gel, which may be provided in the form of a patch, or by use of a cream, foam, and the like. Several gels, patches, creams, foams, and the like appropriate for application to wounds can be modified for delivery of nicotine receptor agonist formulations according to the invention (see, e.g., U.S. Pat. Nos. 5,853,749; 5,844,013; 5,804,213; 5,770,229; and the like). In general, topical administration is accomplished using a carrier such as a hydrophilic colloid or other material that provides a moist environment. Alternatively, for the purpose of wound healing the nicotine agonist could be supplied, with or without other angiogenic agents in a gel or cream the could be applied to the wound. An example of such an application would be as a sodium carboxymethylcellulose-based topical gel with a low bioburden containing the nicotine agonist and other active ingredients together with preservatives and stabilizers.

In other embodiments, the nicotine receptor agonist formulation is delivered locally or systemically, preferably locally, using a transdermal patch. Several transdermal patches are well known in the art for systemic delivery of nicotine to facilitate smoking cessation, and such patches may be modified to provide for delivery of an amount of nicotine receptor agonist effective to stimulate angiogenesis according to the invention (see, e.g., U.S. Pat. Nos. 4,920, 989; and 4,943,435, NICOTROL™ patch, and the like).

In other methods of delivery, the nicotine receptor agonist can be administered using iontophoretic techniques. Methods and compositions for use in iontophoresis are well known in the art (see, e.g., U.S. Pat. Nos. 5,415,629; 5,899,876; 5,807,306; and the like).

The desirable extent of angiogenesis will depend on the particular condition or disease being treated, as well as the stability of the patient and possible side-effects. In proper doses and with suitable administration, the present invention provides for a wide range of development of blood vessels, e.g., from little development to essentially full development.

Stimulation of angiogenesis and/or vasculogenesis by administration of a nicotine receptor agonist can be controlled by administration of compounds that interfere with nicotine receptor agonist-mediated angiogenic stimulation. In this sense, the invention also provides for a means of controlling or inhibiting angiogenesis by interfering with the role of the nicotine in the angiogenic process. This may be accomplished, for example, administration of agents that inhibit the ability of nicotine to mediate its effects through the nicotine receptor (e.g., by inhibiting binding of nicotine to the nicotine receptor). Exemplary nicotinic receptor antagonists include hexamethonium and mecamylamine (formulas provided in FIG. 1). Alternatively, nicotine receptor agonist-mediated angiogenesis can be controlled or inhibited by administration of inhibitors of processes downstream of nicotine receptor signaling. For example, inhibitors of nitric oxide synthase and/or prostacyclin antagonists can be administered to inhibit angiogenesis. The angiogenesis inhibitor may be administered in the same manner and dosages to mammals, such as humans, as described with respect to the nicotine receptor agonist.

Where the subject has had exposure, particularly chronic exposure, to a nicotine receptor agonist (e.g., as in a subject who is a smoker and who has had prior, particularly chronic, systemic exposure to nicotine), the nicotine receptor or other nicotine receptor agonist-binding receptor that mediates stimulation of angiogenesis may be present at lower levels than in subjects who have not had previous exposure or chronic exposure to a nicotine receptor agonist. In such subjects, it thus may be desirable to administer an initial course of a nicotine receptor antagonist to stimulate an increase in nicotine binding-receptors.

Dose

The dose of nicotine or other nicotine receptor agonist administered to a subject, particularly a human, in the context of the present invention should be sufficient to effect a therapeutic angiogenic response in the subject over a reasonable time frame. The dose will be determined by the potency of the particular nicotine receptor agonist employed and the condition of the subject, as well as the body weight of the subject to be treated. For example, the level or affinity or both of the nicotine receptor agonist for the nicotine receptor may play a role in regulating the compound's angiogenic activity. The size of the dose also will be determined by the existence, nature, and extent of any adverse side-effects that might accompany the administration of a particular compound.

In determining the effective amount of nicotine or nicotine receptor agonist in the stimulation of angiogenesis, the route of administration, the kinetics of the release system (e.g., pill, gel or other matrix), and the potency of the nicotine agonist is considered so as to achieve the desired angiogenic effect with minimal adverse side effects. The nicotine receptor agonist will typically be administered to the subject being treated for a time period ranging from a day to a few weeks, consistent with the clinical condition of the treated subject.

The following dosages assume that nicotine is being administered, or a nicotine receptor agonist with similar potency and efficacy as nicotine. As will be readily apparent to the ordinarily skilled artisan, the dosage is adjusted for nicotine receptor agonists according to their potency and/or efficacy relative to nicotine. If given orally or as an inhalant, the dose may be in the range of about 0.01 mg to 10 mg, given 1 to 20 times daily, and can be up to a total daily dose of about 0.1 mg to 100 mg. If applied topically, for the purpose of a systemic effect, the patch or cream would be designed to provide for systemic delivery of a dose in the range of about 0.01 mg to 10 mg. If the purpose of the topical formulation (e.g., cream) is to provide a local angiogenic effect, the dose would likely be in the range of about 0.001 mg to 1 mg. If injected for the purpose of a systemic effect, the matrix in which the nicotine agonist is administered is designed to provide for a systemic delivery of a dose in the range of about 0.001 mg to 1 mg. If injected for the purpose of a local effect, the matrix is designed to release locally an amount of nicotine agonist in the range of about 0.003 mg to 1 mg.

Regardless of the route of administration, the dose of nicotine receptor agonist can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated. In the treatment of some individuals with nicotine receptor agonists, it may be desirable to utilize a "megadosing" regimen. In such a treatment, a large dose of the nicotine receptor agonist is administered to an individual, time is allowed for the compound to act, and then a suitable reagent, e.g., a nicotine receptor antagonist, is administered to the individual to render the active compound ineffective or to reduce its systemic side-effects.

Conditions Amenable to Treatment by Nicotine Receptor Agonist-Mediated induction of Angiogenesis The methods and nicotine receptor agonist-comprising compositions of the invention can be used to treat a variety of conditions that would benefit from stimulation of angiogenesis, stimulation of vasculogenesis, increased blood flow, and/or increased vascularity.

Examples of conditions and diseases amenable to treatment according to the method of the invention include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Other forms of therapeutic angiogenesis include, but are not necessarily limited to, the use of nicotine receptor agonists to accelerate healing of wounds or ulcers; to improve the vascularization of skin grafts or reattached limbs so as to preserve their function and viability; to improve the healing of surgical anastomoses(e.g., as in re-connecting portions of the bowel after gastrointestinal surgery); and to improve the growth of skin or hair.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following is a description of the methods and materials used in the specific examples below.

Animals.

Eight to ten week old female wild type C57BL/6J mice were used. The mice weighed 20–25 grams (Jackson Laboratories, Bar Harbor, ME and Department of Comparative Medicine (DCM), Stanford, Calif.), and were maintained as previously described (Maxwell et al. (1998) *Circulation* 1998 98(4):369–374).

Disc Angiogenesis System (DAS)

To study whether nicotine induces angiogenesis in vivo, we employed the disc angiogenesis system (DAS) (Kowalski et al. (1992) *Exp Mol Pathol* 56(1):1–19; Fajardo et al. (1998) *Lab Invest* 58:718–7244).

Preparation of the Disc.

The DAS consisted of a disc (11 mm in diameter and 1 mm thickness) made of a polyvinyl alcohol sponge (Kanebo PVA, RippeyCo., Santa Clara, Calif.). Both sides were covered with nitrocellulose cell-impermeable filters (Millipore filters, 0.45*m in pore diameter, Millipore, SF, Calif.) of the same diameter as the sponge disc, fixed to the sponge using Millipore glue #1 (xx70000.00, Millipore). As a result, cells(and thus vessels) could penetrate or exit only through the rim of the disc (Kowalski et al. (1992) *Exp Mol Pathol* 56(1):1–19; Fajardo et al. (1998) *Lab Invest* 58:718–7244).

In order to study the local effect of nicotine on angiogenesis, nicotine was placed in a pellet which was added directly to the disc. Briefly, a 1.5-mm core (pellet) was cut from the disc center. Both the pellets and discs were sterilized prior to assembly in a laminar flow hood. The pellet was loaded with up to 20 mcl of the nicotine solution and subsequently air-dried. We placed in the disc pellets with either vehicle (PBS, Sigma, Chemical Co., St Louis, Mo., n=5) or nicotine(10-6 M, Aldrich Chemical Company, Milwaukee, Wis., n=5) to study the effects of locally administered nicotine. For comparison, in some cases basic fibroblast growth factor(bFGF; 20 mcg) or Del-1 protein(0.2 M) was added to the pellet, rather than nicotine. Both bFGF and Del-1 are known to induce angiogenesis. The pellet was then coated with ethylene-vinyl acetate co-polymer (Elvax, Dupont, Chemcentral Corp., Chicago, Ill.) which would permit slow release of the nicotine from the pellet into the disc. The pellet was then re-inserted into the disc before sealing the disc with the millipore filters.

To study the systemic effects of nicotine, in some cases the animals were administered nicotine in their drinking water (see below).

Implantation of the Disc.

The mice were anesthetized with 4% chloralhydrate [intraperitoneal administration (i.p.), 0.1 cc/10 g body weight]. The flanks and posterior surface of the thorax were shaved and cleaned with saturated 70% isopropyl alcohol. A 2-cm incision was made in the skin of the flank contra-lateral to the implantation site. Blunt dissection through the subcutaneous tissue produced a channel into which the saline moistened disc was inserted. The skin was closed with 5.0 silk suture (Kowalski et al. (1992) *Exp Mol Pathol* 56(1): 1–19; Fajardo et al. (1998) *Lab Invest* 58:718–7244).

Disc Removal and Preparation.

Two weeks after disc implantation, the mice were sacrificed with an overdose of 4% chloral hydrate (i.p.) and cervical dislocation. A careful incision was made next to the skin overlying the implanted disc, and the disc was gently removed from the implantation site. Attached tissue was carefully detached from the disc. After removing the disc, one filter was separated from the disc. Discs were then fixed in 10% formalin and embedded flat in paraffin. Subsequently, 5 μm sections were made in a plane through the center of the disc and parallel to the disc surface.

Quantitation of Results.

The disc sections were stained with H&E for light microscopy and histomorphometric measurement of radial growth, and stained with toluidine blue for quantitative determination of total area of fibrovascular growth. Using a video microscope and a computer assisted digital image analysis system (NIH Image 1.59b9), the entire area of fibrovascular growth in the toluidine blue stained disc was calculated and expressed in $mm^2$. As described in a previous study, total fibrovascular growth area is directly proportional to the total area of the disc occupied by blood vessels (Kowalski et al. (1992) *Exp Mol Pathol* 56(1):1–19; Fajardo et al. (1998) *Lab Invest* 58:718–7244). Therefore, the measurement of such total area is used as an index of angiogenesis (Kowalski et al. (1992), supra; Fajardo et al. (1998), supra).

Vascular Continuity Assessment.

To visualize the microvessels in the disc sections and to establish that there was continuity between the systemic and disc vasculatures, luconyl blue dye was injected into the left carotid artery prior to euthanizing the mice. Animals were anesthetized using 4% chloralhydrate (i.p., 0.1 cc/10 g body weight). An incision was made in the ventral midline of the neck. After the carotid sheath was exposed, the left carotid artery was separated from the neurovascular bundle and secured by two 4.0 silk sutures. An incision was made in the carotid and a 15-cm length of PE10 tubing (Beckton Dickinson, Sparks Md.) was introduced into the carotid artery and advanced to the ascending aorta just distal to the aortic valve. About 1.0 ml of luconyl blue was then slowly injected from a 1 ml syringe through the tubing into the thoracic aorta. The presence of blue dye in the fibrovascular network in the disc was detected by light microscopy. Microscopy revealed microvessels lined by a single layer of endothelium and erythrocytes contained within their lumen. Luconyl blue dye was observed throughout the vessels of the disc.

Murine Ischemic Hindlimb Model of Peripheral Arterial Disease (PAD)

Mice were anesthetized with 4% chloral hydrate [intraperitoneal administration (i.p.), 0.1 cc/10 g body weight). The medial surface of both hindlimbs were shaved and then cleaned with betadine solution. A 1.5-cm longitudinal incision was performed, extending from the knee to the inguinal ligament. Through this incision, the superficial femoral artery was dissected free along its length. After the distal ends of both the external iliac and superficial femoral arteries were ligated with 7.0 (Ethicon), complete excision of the femoral artery was performed. An additional set of mice underwent sham operation. The incisions were then closed with discontinuous stitches of 5.0 silk suture (Ethicon). Ampicillin (1 mg/10 gm body weight) intraperitoneal injection was administered after surgical procedure.

Histological Studies.

Tissue Preparation.

Three weeks after surgery, mice were euthanized with an overdose of 4% chloral hydrate (i.p) and cervical dislocation, and the adductor and semimembranous muscles were collected for capillary density assessment. Briefly, a longitudinal incision in the medial thigh was made to expose the entire hindlimb muscle. The adductor and semimembranous muscles were removed and immediately frozen in OCT. Subsequently, sections 5 µm were taken from the mid-region of each muscle in a transverse orientation. The sections were air dried and fixed in acetone.

Capillary Densitometry.

Immunohistochemistry was performed using an alkaline phosphatase assay to identify the endothelial cells. An eosin counterstain was used to differentiate myocytes. Capillaries and myocytes were identified and counted using light microscopy (20×). For each section, four different fields were selected and the total number of capillaries and myocytes per field determined. These values were averaged to provide a determination of capillary density for each experimental limb. To ensure that value for capillary density was not overestimated due to muscle atrophy, or underestimated due to interstitial edema, capillary density was expressed as a ratio of capillaries to myocytes present in the same field.

Data Analysis

All data are given as mean +/−SEM. Statistical significance was tested using unpaired, two-tailed t-test for comparisons between groups. Statistical significance was accepted for $p<0.05$.

Example 1

Systemic Effect of Nicotine Upon Angiogenesis in vivo

To study the effects of nicotine in systemically treated mice, nicotine (60 mcg/ml, n=5) was diluted in the drinking water. The mechanism of nicotine-induced angiogenesis was studied by giving oral supplementation of indomethacin (20 mcg/ml, Sigma, n=5) and/or LNNA (6 mg/ml, Sigma, n=5) to mice having an implanted DAS both locally treated (nicotine inside the DAS) and systemically treated (nicotine diluted in drinking water). Concentrations of nicotine, indomethacin, and LNNA were determined in accordance to studies using oral supplementation of these agents in murine models (Maxwell et al. (1998) *Circulation* 1998 98(4): 369–374; Fulton et al. (1980) *Int J Cancer* 26(5):669–73; Rowell et al. (1983) *J Pharmacological Methods* 9:249–261).

Figure 2:
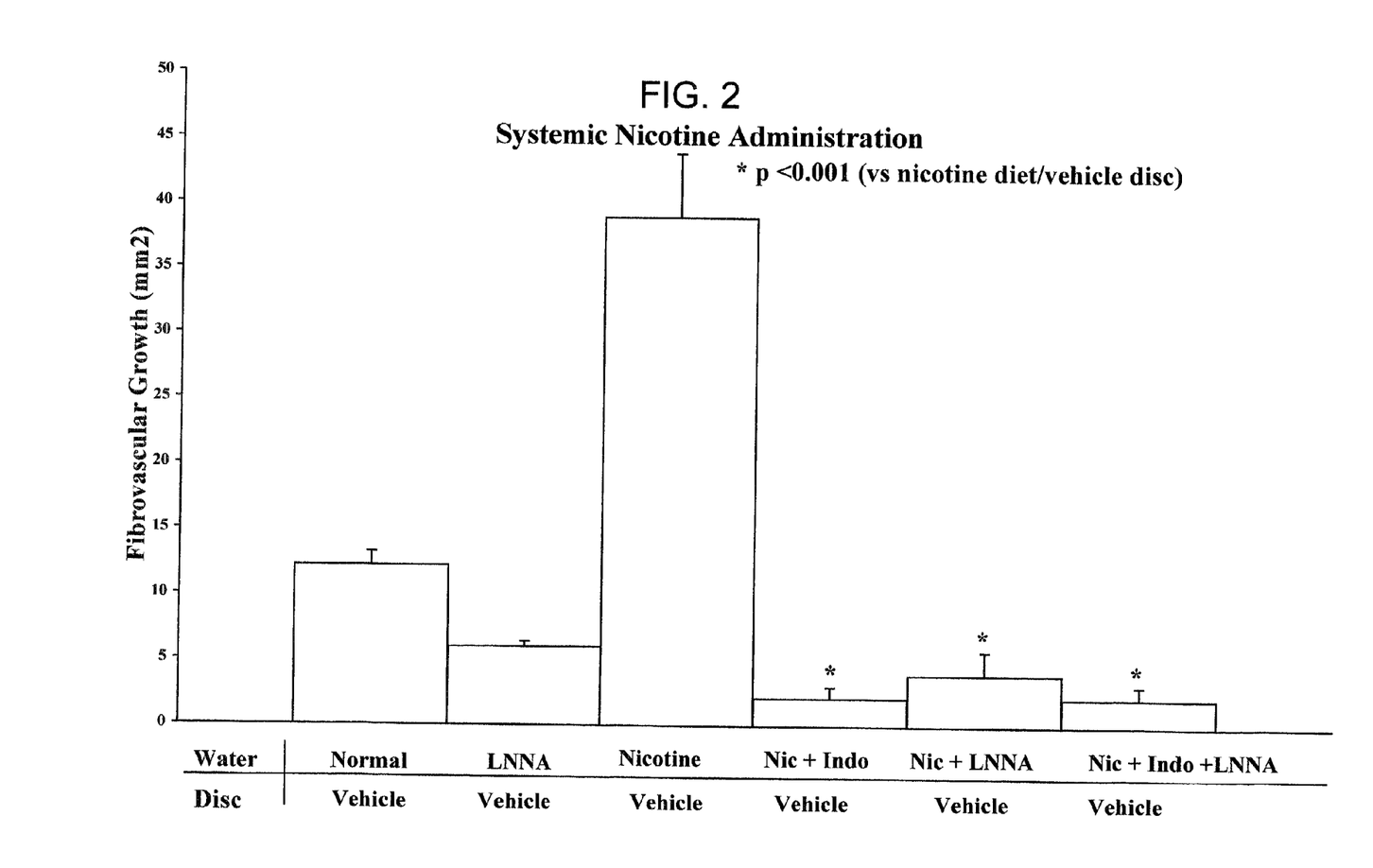
FIG. 2 is a graph illustrating the effect of oral nicotine upon fibrovascular growth in an animal model.

Under basal conditions (untreated water, vehicle-treated disc), fibrovascular growth into the disc occurred. Vessels could be seen growing into the disc. These vessels were in continuity with the systemic circulation as manifested by the influx of leuconyl dye into the disc vasculature, after systemic administration of the dye. The area of the fibrovascular growth into the disc under basal conditions was somewhat greater than 10 mm$^2$ (FIG. 2). With systemic administration of nicotine, there was a dramatic increase in fibrovascular growth with an area of 35 mm$^2$ (FIG. 2). The effect of nicotine was blocked by the NO synthase inhibitor L, nitro-arginine (LNNA) as well as by indomethacin, indicating that synthesis of both nitric oxide and prostacyclin were required for the angiogenic effect of nicotine.

Example 2

Local Effect of Nicotine Upon Angiogenesis in vivo

Figure 3:
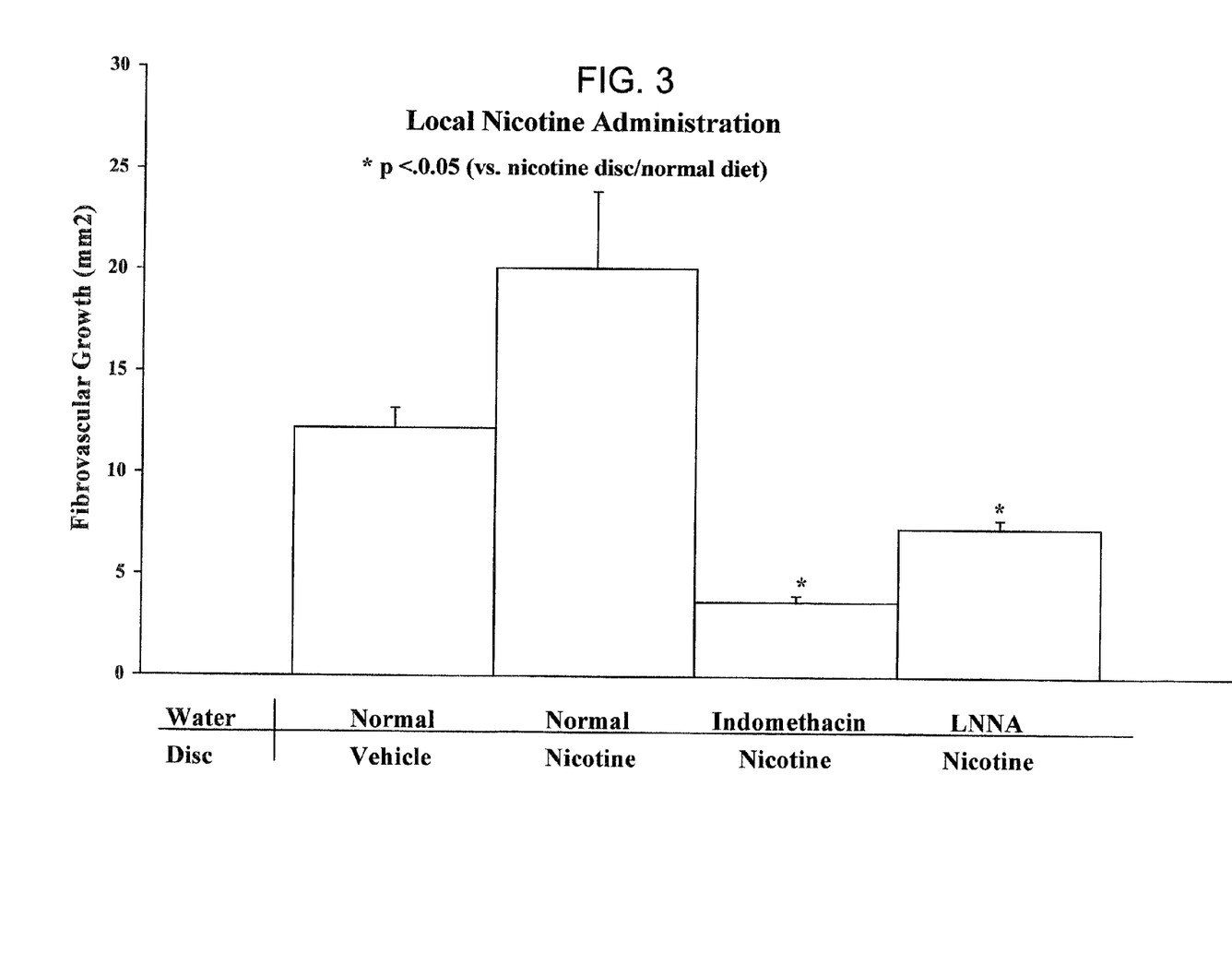
FIG. 3 is a graph illustrating the effect of locally administered nicotine upon fibrovascular growth in an animal model using the disc angiogenesis system.

In order to determine if local administration of L-arginine could be effective at inducing angiogenesis, in some animals, nicotine was placed within a pellet that was inserted into the disc angiogenesis system (described above). When nicotine was placed in the disc (rather than administered in the water of the animals as described in Example 1) a similar effect was observed. The fibrovascular growth under basal conditions (about 10 mm$^2$) was increased to about 20 mm$^2$ (FIG. 3). Again, indomethacin or LNNA blocked the effects of nicotine. These studies indicate that systemic or local administration of nicotine induces angiogenesis.

Example 3

Comparison of Effects of Nicotine with Other Angiogenic Agents

Figure 4:
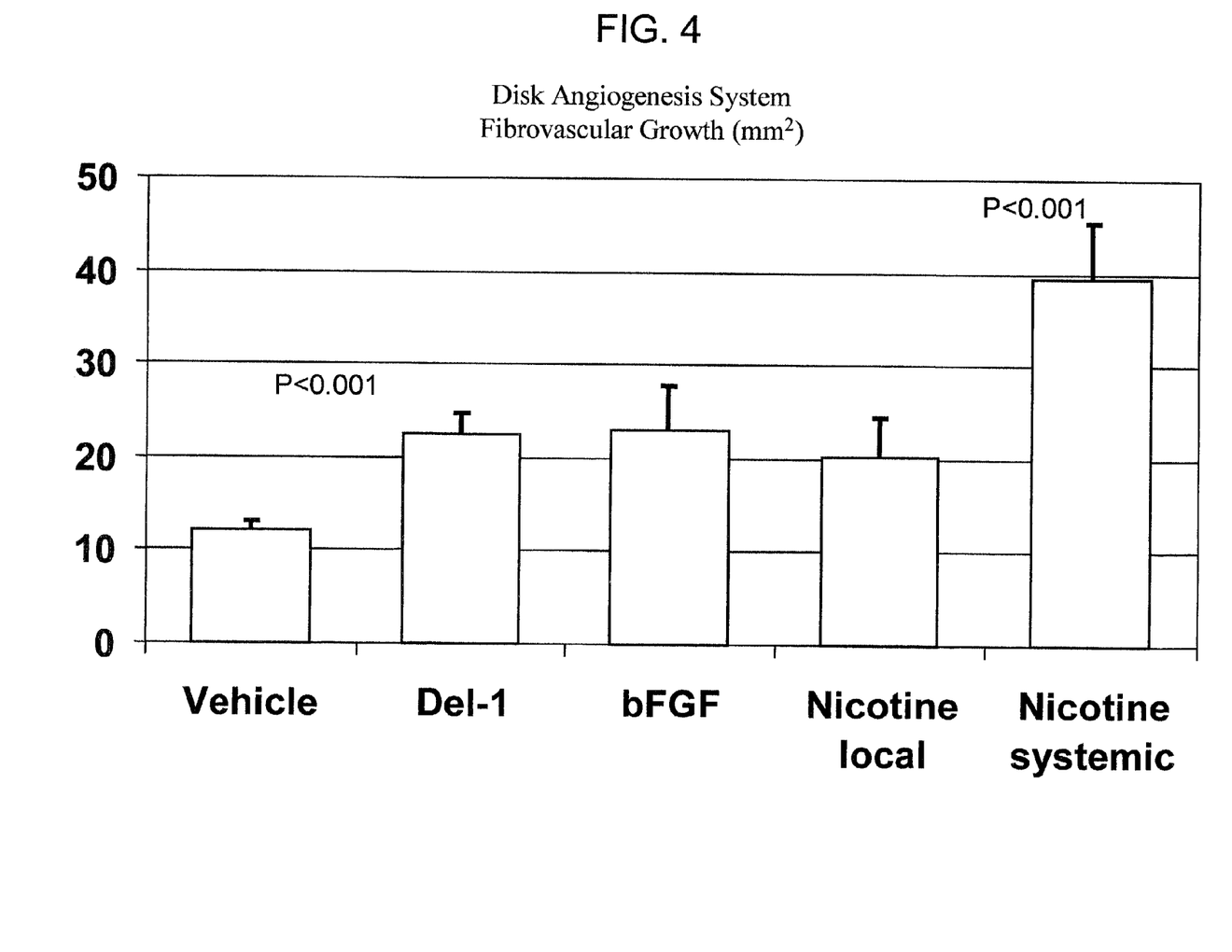
FIG. 4 is a graph illustrating comparing the relative angiogenic potencies of the angiogenic factors Del-1 and bFGF with locally or systemically administered nicotine.

The effects of nicotine were compared with the angiogenic agents bFGF and Del1. The comparison with bFGF is particularly important because this agent is already in clinical trials in humans for therapeutic angiogenesis. In comparison to vehicle, bFGF, Del1, and nicotine each increased angiogenesis to the same degree. Systemically administered enhance angiogenesis to a much greater degree than locally administered bFGF and Del-1 (FIG. 4). Paradoxically, the effect of systemic nicotine administration was greater than local nicotine administration, even though systemic nicotine administration undoubtedly produced lower local levels in the disc. The paradox may be explained by the experiments shown below where it was observed that intermediate doses of nicotine administered intramuscularly have the greatest effect. At higher intramuscular doses of nicotine, less angiogenesis is observed.

Example 4

Figure 5:
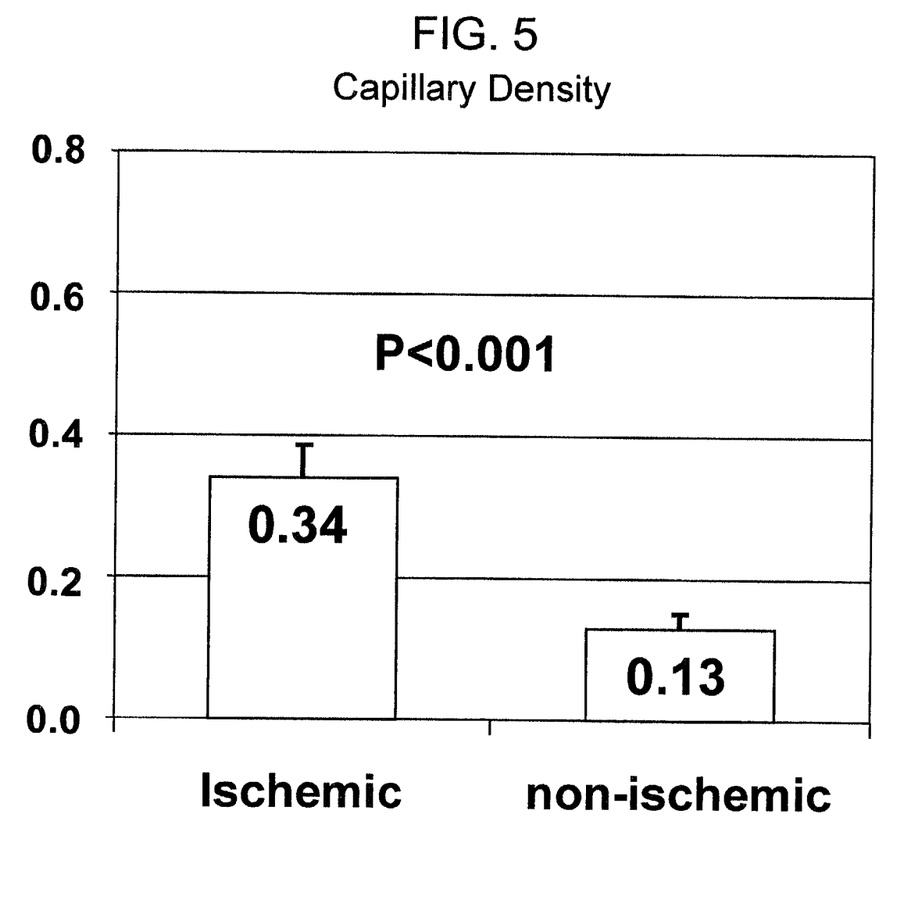
FIG. 5 is a graph illustrating the relative capillary densities in non-ischemic (control; "non-ischemic") ischemic limbs in the hindlimb ischemia model ("ischemic").

Induction of Angiogenesis in the Murine Hindlimb Ischemia Model of Peripheral Arterial Disease To provide more compelling evidence for the therapeutic angiogenic effects of nicotine, the angiogenic effects of nicotine were examined in a model of arterial occlusive disease, the murine ischemic hindlimb (described above). Daily intramuscular injections of nicotine solution or vehicle were administered (50 µl) for a period of three weeks. Five groups of animals received 0, 3, 30, 300 or 3200 ng/kg of nicotine by intramuscular injection daily (represented in FIGS. 6 and 7 as 1× (0.0811 ng nicotine in 50 µl saline (=0.003 µg/kg), 10× (0.811 ng nicotine in 50 µl saline (=0.03 µg/kg), 100× (8.11 ng nicotine in 50 µl saline (=0.3 µg/kg), and 1000× (81.1 ng nicotine in 50 µl saline (=3.2 µg/kg)). As shown in FIG. 5, 3 weeks after surgery, capillary density (capillaries/myocyte) was increased in operated limbs (ischemic) in comparison to non-operated limbs (non-ischemic) consistent with a basal angiogenic response to ischemia.

Figure 6:
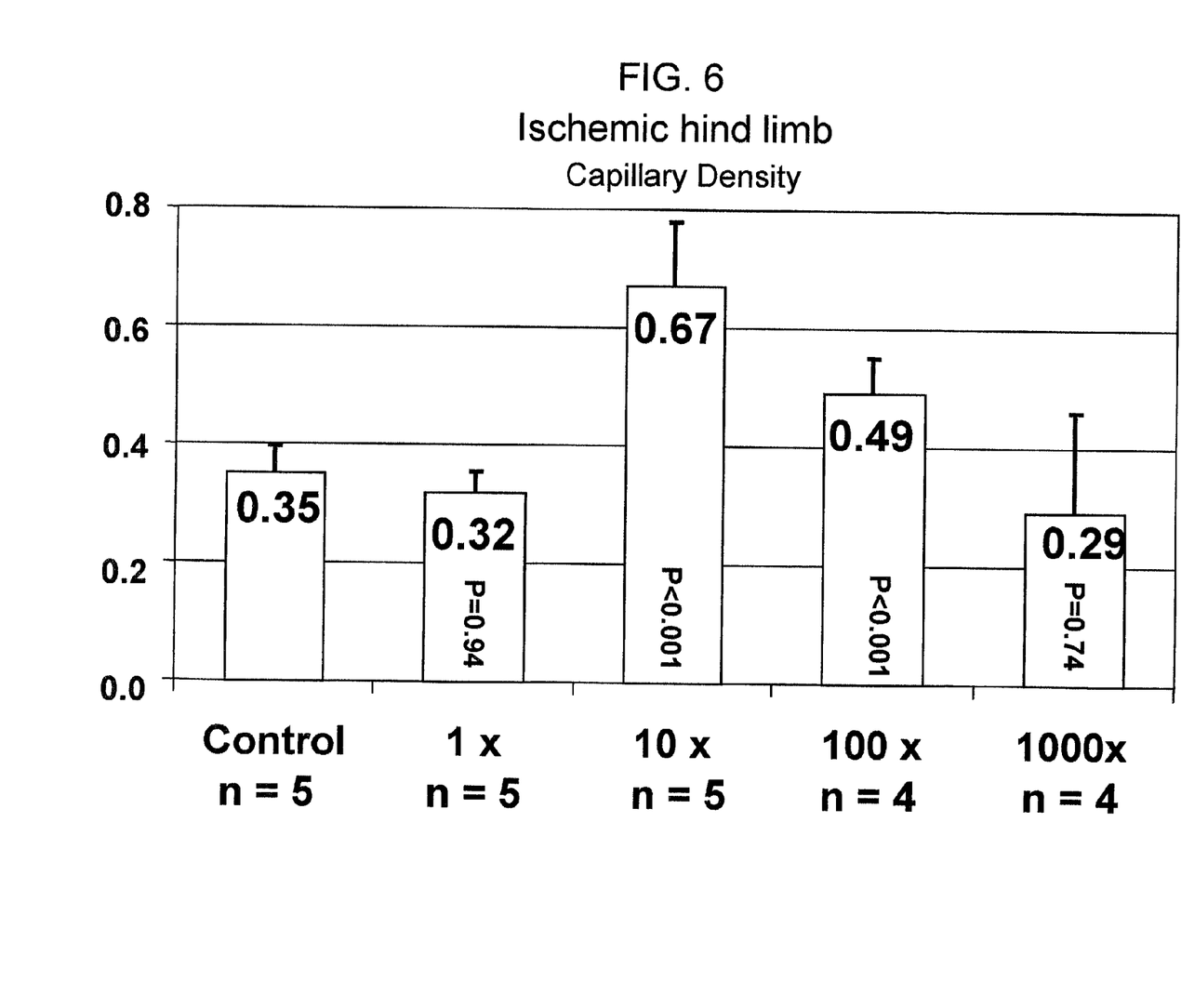
FIG. 6 is a graph illustrating the effect of intramuscularly administered nicotine upon capillary density in an animal model of ischemia.
Figure 7:
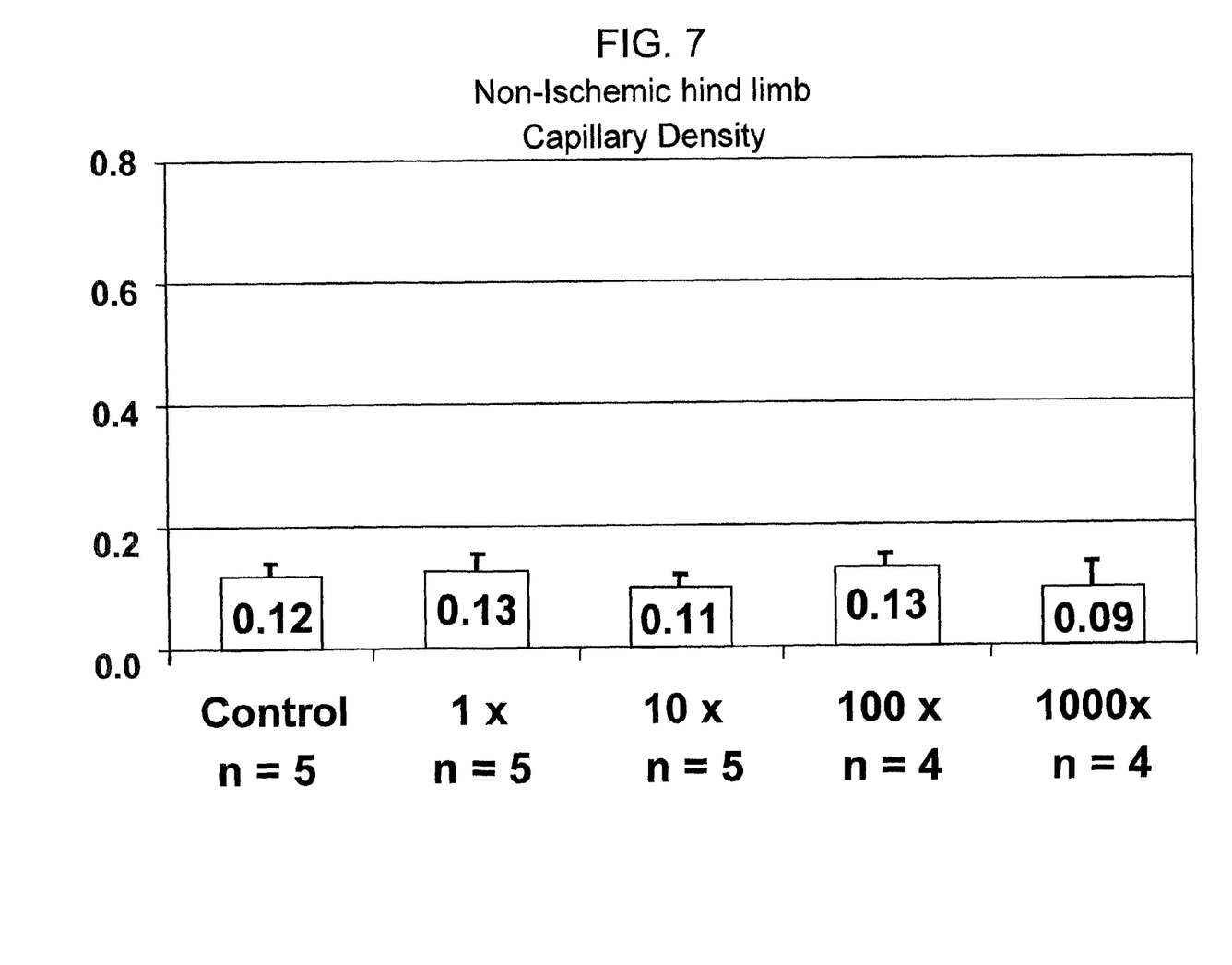
FIG. 7 is a graph illustrating the effect of intramuscularly administered nicotine upon capillary density in an untreated, non-ischemic limb of an animal of FIG. 6.

As shown in FIGS. 6 and 7, nicotine enhanced the angiogenic response to ischemia relative to controls. With vehicle control, 0.35 capillaries/myocyte were detected in the ischemic limb. At an intermediate dose of 0.03 µg/kg, nicotine nearly doubled angiogenic response (to 0.67 capillaries/myocyte). At the highest dose of nicotine, angiogenesis was not increased; indeed at this dose some toxicity was observed, with evidence of interstitial edema and myocyte necrosis. The angiogenic effect remained local to the site of nicotine injection, since no angiogenic effect was detected in a non-ischemic hindlimbs (FIG. 6). Thus, local intramuscular administration of these doses of nicotine did not result in a systemic angiogenic effect.

These studies indicate that nicotine enhances angiogenesis in a murine model of human peripheral arterial disease, and that nicotine receptor agonists are useful for therapeutic angiogenesis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for increasing blood flow to ischemic tissue in a mammalian subject, the method comprising:
    administering to the subject an amount of a nicotine receptor agonist effective to stimulate angiogenesis and increase blood flow to the ischemic tissue.
2. The method of claim 1, wherein said administering is by use of a catheter.
3. The method of claim 2, wherein the catheter is a balloon catheter.
4. The method of claim 1, wherein said administering is by injection of the nicotine receptor agonist into a vessel wall at or proximate to the ischemic tissue.

* * * * *